United States Patent [19]
Gold

[11] Patent Number: 4,534,363
[45] Date of Patent: Aug. 13, 1985

[54] COATING FOR ANGIOGRAPHIC GUIDEWIRE

[75] Inventor: Philip Gold, Pompano Beach, Fla.

[73] Assignee: Cordis Corporation, Miami, Fla.

[21] Appl. No.: 604,399

[22] Filed: Apr. 26, 1984

Related U.S. Application Data

[63] Continuation of Ser. No. 372,900, Apr. 29, 1982, abandoned.

[51] Int. Cl.³ .............................................. A61B 5/02
[52] U.S. Cl. ................................... 128/772; 604/265
[58] Field of Search .................. 128/772, 657, 658; 604/51, 52, 53, 264, 265–268

[56] References Cited

U.S. PATENT DOCUMENTS

| | | | |
|---|---|---|---|
| 3,416,531 | 12/1968 | Edwards | 128/772 |
| 3,485,234 | 12/1969 | Stevens | 128/657 |
| 3,509,883 | 5/1970 | Dibelius | 604/264 |
| 3,574,673 | 4/1969 | Schweiger | 117/132 |
| 3,605,725 | 8/1968 | Bentov | 128/2.05 R |
| 3,922,378 | 11/1975 | Kline | 128/772 |
| 3,924,632 | 12/1975 | Cook | 128/772 |
| 3,973,556 | 6/1975 | Fleischhacker et al. | 128/2 M |
| 4,003,369 | 1/1977 | Heilman et al. | 128/772 |

OTHER PUBLICATIONS

"Siliconizing Intestinal Decompression Tubes" Cantor, *American J. Surgery* vol. 100, 10-1960.

*Primary Examiner*—Edward A. Miller
*Assistant Examiner*—T. J. Wallen
*Attorney, Agent, or Firm*—Henry W. Collins; Thomas R. Vigil

[57] ABSTRACT

There is disclosed an improved coating for an angiographic guidewire and a method of manufacturing the guidewire. The guidewire takes the form of a coiled wire which is coated with copolymers of methylsiloxane and aminoalkylsiloxane units to enhance the lubricity of the guidewire when it is inserted into a catheter.

6 Claims, 2 Drawing Figures

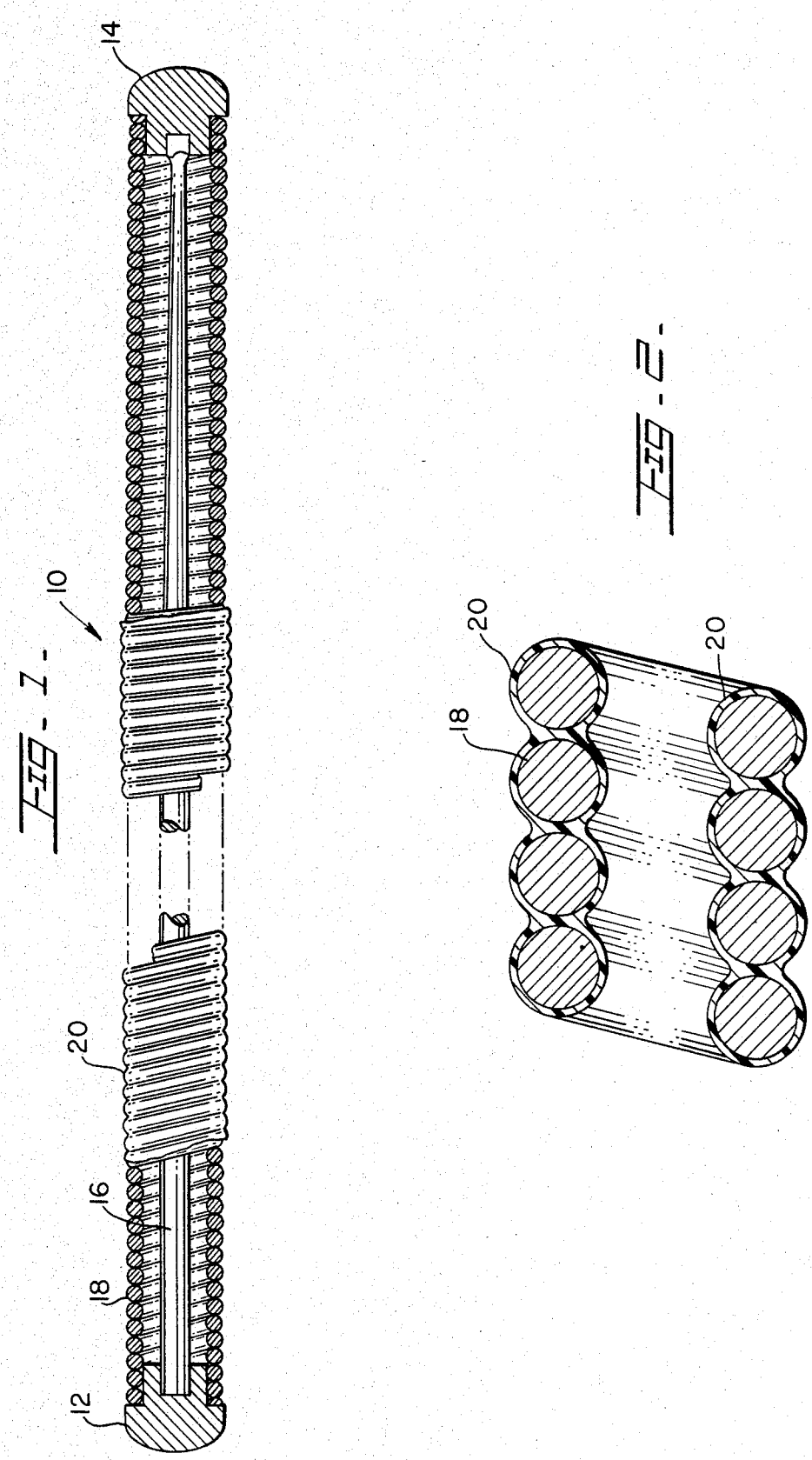

COATING FOR ANGIOGRAPHIC GUIDEWIRE

This is a continuation of application Ser. No. 372,900 filed Apr. 29, 1982 now abandoned.

BACKGROUND OF THE INVENTION

This invention relates to coated guidewire for use in catheters. The guidewires are coated with organosiloxane copolymer.

Guidewires for catheters have been coated with lubricants such as Teflon prior to winding the guidewire into a coiled form. When the coated wire has been tightly wound into an elongated coil, a safety core wire is inserted into the coil and is welded to the respective ends of the guidewire. The safety core wire generally takes the form of a cylindrical wire having a uniform main body which is smoothly tapered into a very flexible flattened tip so that one end of the guidewire exhibits the property of being rigid and the other end of the guidewire remains very flexible.

In inserting a catheter into the vascular system of a patient, the guidewire is initially inserted through a cannula into the vascular system, the cannula is removed, and the catheter is inserted over the guidewire. The catheter is then moved along the guidewire to the desired position within the vascular system and the guidewire is removed. Once the guidewire has been removed, the catheter is in condition for use.

Accordingly, the guidewire must be extremely flexible at the distal end so that the guidewire may be initially moved through the vascular system to a position where it is desired to insert the cannula. The proximal end of the guidewire should remain relatively rigid so that the position of the guidewire may be controlled upon insertion of the guidewire within the vascular system. It is, therefore, desirable that the guidewire have a flexible distal tip and a relatively stiff body portion. In addition, the guidewire should have a very smooth and lubricious outer surface.

Guidewires generally take the form of a tightly wound spring which is constructed of a very fine wire tightly wrapped to form a coil in which all of the turns contact adjacent turns. It is important that the guidewire surface be as smooth as possible so that the internal walls of the vascular system are not traumtized or damaged during movement of the guidewire through the vascular system.

As is apparent, any material introduced into the bloodstream has the potential of initiating blood clots. Since blood clots are an undesirable side effect of known angiographic guidewires, it is desirable to utilize materials which eliminate the probability of the formation of blood clots and include a surface which is as lubricious as possible thereby preventing trauma to the blood vessel.

One approach to preventing blood clot formation is the use of a guidewire surface which is coated with Teflon prior to winding to provide a relatively smooth antithrombogenic surface. Such a Teflon coated angiographic guidewire is disclosed in U.S. Pat. No. 4,003,369.

While Teflon coated guidewires provided a substantial improvement over previously developed guidewires, the guidewire of the present invention has with improved lubricity with reduced trauma to the blood vessel system.

As will be described in greater detail hereinafter, the guidewire of the present invention is coated with an organisiloxane copolymer to provide the enhanced lubricity with reduced trauma to a blood vessel system. Such a copolymer has been proposed for use as a coating for a fine cutting edge in U.S. Pat. No. 3,574,673. However, heretofore, such a copolymer has not been proposed as a coating for an angiographic guidewire.

SUMMARY OF THE INVENTION

Briefly, the present invention is directed toward a guidewire having a wound outer casing which is coated with an organosiloxane copolymer. The guidewire also includes an integral core wire for insuring structural integrity of the guidewire without substantially reducing the flexibility of the distal tip of the guidewire. The invention also relates to a method of manufacturing the guidewire of the present invention.

As a final operation after the guidewire is completely fabricated, the core wire is then inserted into the outer casing and is attached to the casing at the distal and proximal ends. The distal tip of the core wire is tapered to a very small cylindrical cross-sectional area in order to make the guidewire very flexible at the distal tip.

The smooth outer surface of the wound guidewire is developed by coating the coiled guidewire with copolymers of methylsiloxane and aminoalkylsiloxane units, such as

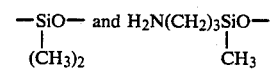

Accordingly, the present invention produces a smooth guidewire which is very lubricious and which includes an integral core wire which is relatively rigid at the proximal end and is very flexible at the distal end.

Accordingly, the primary object of the present invention is to provide a guidewire having an ultrasmooth exterior surface.

A further object of the present invention is to provide a wire wound guidewire having an outer surface which is coated with a lubricating material which is biocompatible with blood.

Still a further object of the present invention is to provide a method of fabricating a guidewire with an improved coating.

These and other objects of the present invention, as well as the attendant advantages thereof, will become more readily apparent when reference is made to the following description taken in conjunction with the accompanying drawings.

BRIEF DESCRIPTION OF THE DRAWINGS

FIG. 1 is a perspective view of an embodiment of the guidewire of the present invention; and FIG. 2 is a cross-sectional view of a portion of the guidewire shown in FIG. 1 and illustrates the lubricating coating in more detail.

DESCRIPTION OF THE PREFERRED EMBODIMENT

An elongated guidewire 10 constructed in accordance with the teachings of the present invention is illustrated in FIG. 1. The guidewire 10 includes an elongated body with a proximal tip portion 12 and a distal tip portion 14. A core wire 16 extends from the proximal end 12 to the distal end 14 of the guidewire 10.

The outer core of the guidewire takes the form of a coil spring 18, which is wound from thin wire with each of the coils in direct contact with adjacent coils. The core 16 is welded to the proximal tip portion 12 and is welded to the distal tip portion 14. The tip portions 12, 14 serve to retain the respective ends of the wound body of the coil spring 18.

As is illustrated, the core wire 16 is of an elongated cylindrical configuration and tapers from the proximal end to the distal end of the guidewire. As is apparent, the core wire 16 serves to impart rigidity to the guidewire at the proximal end of the guidewire, however, the core wire 16 does not substantially reduce the flexibility of the coil spring 18 at the distal end of the guidewire.

When the guidewire 10 has been assembled as illustrated in FIG. 1, a lubricating coating 20 is applied to the coil spring 18. The coating may be applied by simply dipping the guidewire in a solution of the lubricating coating, by wiping the coating onto the external surface of the guidewire or by spraying the guidewire with a lubricating coating.

As illustrated in FIG. 2, because of the low viscocity of the lubricating coating 20, the coating passes between adjacent turns of the coil spring 18 and completely surrounds each of the turns of the coil spring 18. With this smooth lubricious coating of the coil spring 18, the coating serves the function of reducing the formation of blood clots because of the smooth outer surface of both the outer portion and inner portion of the coil spring 18.

The lubricating coating takes the form of an adherent coating consisting essentially of at least a partially cured organosiloxane copolymer consisting of:

(1) 5 to 20 weight of polymeric units of the formula

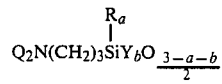

in which
R is a lower alkyl radical containing no more than 6 carbon atoms;
Y is selected from the group consisting of 13 OH and —OR' radicals, in which R' is an alkyl radical of no more than 3 carbon atoms;
Q is selected from the group consisting of the hydrogen atom, —CH$_3$ and —CH$_2$CH$_2$NH$_2$;

a has a value of 0 or 1; and
b has a value of 0 to 1; the sum of a+b being from 0 to 2; and
(2) 80 to 95 weight percent of polymeric units the formula

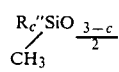

in which
R" is selected from the group consisting of —OH and —CH$_3$ radicals, and c has a value of 1 or 2.

As described above, the aminoalkyl siloxane unit can contain lower alkyl substituents, such as methyl, ethyl, propyl, t-butyl and hexyl radicals. In addition, those copolymers which are not fully condensed will contain hydroxyl or alkoxy substituents, such as methoxy, ethoxy, and propinoxy radicals. The Q substituents bonded to the nitrogen atom can be the same or different. Thus the aminoalkysiloxane units include

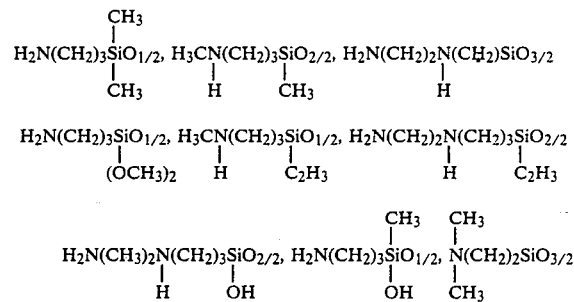

and the like.
The methylsiloxane units of the copolymer include

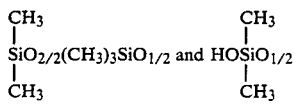

The copolymers utilized in the practice of the invention are commercially available and are prepared by well known methods, such as cohydrolysis and co-condensation or equilibration of aminoalkyl-substituted aminoalkyl polysiloxane with dimethylpolysiloxane in the presence of an alkaline equilibration catalyst.

A preferred method of preparation is discussed in detail in U.S. 3,355,424, the disclosure of which is incorporated herein by reference. In brief this method comprises mixing the appropriate molar amounts of (polyaminoalkyl)-alkoxysilane, Q$_2$N(CH$_2$)$_3$SiR$_a$(OR)$_{3-a}$ with a conventional dimethylpolysiloxane which contains a substantial amount of silicon-bonded hydrosyl groups, for example, 1 to 5 percent by weight ≡ SiOH. The reaction to form new siloxane bonds is illustrated as follows:

The reaction rate is accelerated by heating in the range of 100° to 200° C. Inert solvents can be present if desired. The alcohol which is formed in this reaction can be removed by distillation, thus it is certain that true copolymers are formed. It is apparent that the copolymer can have unreacted (OR') and/or (OH) groups present, depending upon the relative amounts of reactants and the amount of (OR') and (OH) present in the reactants initially. If desired, excess (OR') groups can be hydrolyzed by the addition of water to the system. Controlling the amount of water so added controls the amount of such groups remaining in the copolymer. Likewise, excess (OH) groups can be caused to condense, as for example by heating the copolymer. Any or all of the alcohol formed by either the reaction or by subsequent hydrolysis can be left in the reaction product if desired.

The copolymeric coating is in the form of a stable material coating 20 which is adherent to the underlying surface of the coiled spring 18. As used in this specification "at least partially cured copolymer" is defined as a crosslinked or partially crosslinked copolymer which has insoluble, infusible coherent three-dimensional structure, within which an uncured or partially cured fluid copolymer is contained. The material is relatively soft and waxy as contrasted to hard vitreous resins, which develop fractures when coated onto a hard surface.

The liquid copolymer is applied to the guidewire 10 in any suitable manner, for example by dipping brushing or spraying the material onto the coil spring 18. The copolymer may be applied with a solvent carrier, such as isopropyl alcohol. Prior to applying the copolymer, the coil spring 18 should be carefully cleaned so as to remove any oils which may have formed on the surface. This cleaning process can be accomplished by use of any suitable solvent.

When the copolymer has been applied to the surface, the copolymer may be cured by heating the guidewire for a short period of time (e.g. 30 minutes at 120° C.) or by exposing the guidewire to room temperature and 50% relative humidity conditions for a longer period of time.

In evaluating the guidewire of the present invention, tests have shown that the improved lubricating coating adheres satisfactorily to the coil spring 18 and that the coating exhibits improved lubricity over existing guidewires and with reduced trauma to a blood vessel system.

Reasonable modifications and variations are within the teachings of the invention as set forth in the following claims for an improved guidewire for catheters and method of manufacturing such guidewires.

I claim:

1. An angiographic guide wire adapted to guide a catheter into the body of a patient; said guide wire comprising: an elongate wire which has a circular cross-section and which is wound into a coil spring of consecutive adjacent coils; a proximal tip fixed ot one end of said coiled wire; a distal tip fixed to the other end of said coiled wire; a core wire fixed to and between the tips; and a thin continuous coating of low friction, slippery material completely encasing and interconnecting said coiled wire and the individual coils thereof, and extending between adjacent coils, said coating consisting essentially of an organosiloxane copolymer.

2. A guidewire as defined in claim 1 wherein said organisiloxane copolymer consists of
   (a) 5 to 20 weight percent of polymeric units of the formula

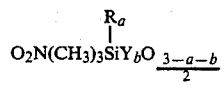

in which
   R is a lower alkyl radical containing no more than 6 carbon atoms;
   Y is selected from the group consisting of —OH and OR' radicals, in which R' is an alkyl radical of no more than 3 carbon atoms;
   Q is selected from the group consisting of the hydrogen atom, —CH$_3$ and —CH$_2$CH$_2$NH$_2$;
   a has a value of 0 to 1; and
   b has a value of 0 or 1; the sum of a+b being from 0 to 2; and
   (b) 80 to 95 weight percent of polymeric unit of the formula

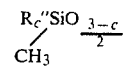

in which
R" is selected from the group consisting of —OH and —CH$_3$ radicals; and
c has value of 1 or 2.

3. The guidewire defined in claim 2 wherein the polymeric units (a) are of the formula:

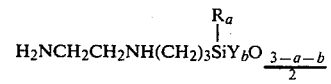

wherein
R is a lower alkyl radical containing no more than 6 carbon atoms;
Y is selected from the group consisting of —OH and —OR' radicals, in
which R' is an alkyl radical of no more than 3 carbon atoms;
a has a value of 0 to 1; and
b has a value of 0 to 1; the sum of a+b being from 0 to 2.

4. The guidewire defined in claim 2 wherein the polymeric units (a) are of the formula

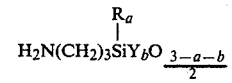

wherein
R is a lower alkyl radical containing no more than 6 carbon atoms;
Y is selected from the group consisting of —OH and —OR' radicals, in which R' is an alkyl radical of no more than 3 carbon atoms;
a has a value of 0 to 1; and
b has a value of 0 to 1; the sum of a+b being from 0 to 2.

5. The guidewire defined in claim 2 wherein the polymeric units (1) are of the formula

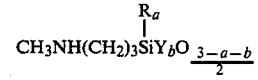

wherein
R is a lower alkyl radical containing no more than 6 carbon atoms; Y is selected from the group consisting of —OH and OR' radicals, in which R' is an alkyl radical of no more than 3 carbon atoms;
a has a value of 0 or 1; and
b has a value of 0 or 1; the sum of a+b being from 0 to 2.

6. The guidewire defined in claim 2 wherein said copolymer consists of approximately 10 weight percent of units of the formula H$_2$NCH$_2$CH$_2$NH(CH$_3$)$_2$SiO$_{3/2}$ and 90 weight percent of units of the formula (CH$_3$)$_3$SiO$_{2/2}$ said copolymer being end blocked with (CH$_3$)$_3$SiO— units.

* * * * *